(12) United States Patent
Vardi et al.

(10) Patent No.: US 6,197,765 B1
(45) Date of Patent: Mar. 6, 2001

(54) USE OF DIAZOXIDE FOR THE TREATMENT OF METABOLIC SYNDROME AND DIABETES COMPLICATIONS

(76) Inventors: Pnina Vardi; Latifa Morad, both of Haifa (IL)

( * ) Notice: Subject to any disclaimer, the term of this patent is extended or adjusted under 35 U.S.C. 154(b) by 0 days.

(21) Appl. No.: 09/327,965

(22) Filed: Jun. 8, 1999

(51) Int. Cl.[7] .............................................. A61K 31/5415
(52) U.S. Cl. ......................................................... 514/223.2
(58) Field of Search ........................................... 514/223.2

(56) References Cited

U.S. PATENT DOCUMENTS

| | | | |
|---|---|---|---|
| 5,284,845 | 2/1994 | Paulsen | 514/223.2 |
| 5,889,002 | 3/1999 | Nielsen et al. | 514/222.8 |

FOREIGN PATENT DOCUMENTS

97/00301  10/1997  (WO) .

OTHER PUBLICATIONS

Valverde et al., Diabetes Research, 10(2), 59–62 (abstract), Feb. 1989.*
Alemzadeh et al., J. Clin. Endocrinol. Metab., 83(6), 1911–1915 (abstract), 1998.*

* cited by examiner

*Primary Examiner*—Phyllis G. Spivack
(74) *Attorney, Agent, or Firm*—Mark M. Friedman

(57) ABSTRACT

The present invention discloses a treatment for syndrome-X, and resulting complications, that include hyperlipidemia, hypertension, central obesity, hyperinsulinemia and impaired glucose intolerance. Diabetic complications include excess proinsulin levels.

23 Claims, No Drawings

USE OF DIAZOXIDE FOR THE TREATMENT OF METABOLIC SYNDROME AND DIABETES COMPLICATIONS

FIELD AND BACKGROUND OF THE INVENTION

The present invention relates to a novel treatment for metabolic syndrome and resulting complications, such as obesity, hypertension, hyperlipidemia, hyperinsulinemia and impaired glucose tolerance. In addition, it concerns the use of diazoxide for the treatment of syndrome-X and resulting complications, as well as diabetic complications.

Oral diazoxide (7-chloro-3-methyl-2H-1,2,4-benzothiadiazine 1,1-diazoxide) is a nondiuretic congener of the thiazide diuretics which inhibits insulin release from the pancreas (ref. 1). Diazoxide was originally developed for the treatment of hypertension. One of the adverse affects of diazoxide was found to be hyperglycemia, which proved useful in the treatment of hypoglycemia. The hyperglycemia caused by diazoxide is usually transitory and is due to decreased insulin secretion and decreased peripheral utilization of glucose (ref. 2). Diazoxide is now used primarily for the treatment of hypoglycemia due to hyperinsulinism, associated with conditions such as inoperable islet cell adenoma or carcinoma (ref. 3). The drug is currently marketed in the U.S. under the tradename Proglycem.

Syndrome-X is a metabolic syndrome. The term syndrome-X was given by Reaven et al describing a condition characterized by central obesity, and metabolic manifestations including resistance to insulin stimulated glucose uptake, hyperinsulinemia, glucose intolerance (not necessarily diabetes), increased level of very low density lipoprotein triglyceride (VLDL), decreased level of high density lipoprotein cholesterol (HDL) concentrations and hypertension (refs. 4, 5). Each of these characteristic features are considered to be risk factors for development of atherosclerosis and other 'old age' diseases. It is believed that syndrome-X is caused by insulin resistance, but no treatment is available at present.

U.S. Pat. No. 5,284,845 discloses the use of oral diazoxide for the normalization of blood glucose and insulin levels in disorders of hyperinsulinemia and diabetes.

However, the background art does not suggest the use of diazoxide for the treatment of syndrome-X, nor for diabetes complications.

No treatment is available for syndrome-X and thus there is a widely recognized need for a drug such as is described in the present invention which is effective in the possible prevention and treatment of syndrome-X and diabetes complications.

SUMMARY OF THE INVENTION

The present invention provides a drug for the treatment of metabolic syndrome, related complications and diabetes complications. Preferably, the present invention provides diazoxide to inhibit the release of insulin and proinsulin, lower weight, reduce levels of circulating cholesterol and triglycerides, lower blood pressure and prevent and reverse diabetic complications in subjects with a metabolic syndrome such as syndrome-X, or with diabetes complications.

According to the teachings of the present invention there is provided in a first embodiment a method for treating syndrome-X and resulting complications in a subject, comprising the step of administering to the subject, a pharmaceutically effective amount of diazoxide.

In a preferred embodiment the complication is selected from the group consisting of central obesity, hyperlipidemia, hyperinsulinemia, hypertension and impaired glucose tolerance.

In a preferred embodiment the pharmaceutically effective amount is from about 4 mg/kg to about 15 mg/kg.

In a preferred embodiment the pharmaceutically effective amount is from about 5 mg/kg to about 8 mg/kg.

In a preferred embodiment the diazoxide is provided in a tablet form.

In a preferred embodiment the diazoxide is provided in an intravenous form.

In a preferred embodiment the preferred route of administration is oral.

In a preferred embodiment the diazoxide is administered until endogenous insulin levels are lowered.

In a preferred embodiment exogenous insulin must be administered.

In a preferred embodiment the diazoxide decreases proinsulin levels.

In a second embodiment, the present invention provides a method for prophylactic treatment of syndrome-X in a subject, comprising the step of administering to the subject a pharmaceutically effective amount of diazoxide.

In a third embodiment, the present invention provides a method for reducing the release of insulin and proinsulin in a subject with syndrome-X, comprising the step of administering to the subject a pharmaceutically effective amount of diazoxide.

In a preferred embodiment the method for reducing the release of insulin and proinsulin in a subject with syndrome-X, further comprises the step of administering exogenous insulin.

In a fourth embodiment, the present invention provides a method for reducing weight in a subject with syndrome-X, comprising the step of administering to the subject a pharmaceutically effective amount of diazoxide.

In a fifth embodiment the present invention provides a method for reducing the levels of circulating cholesterol and triglycerides in a subject with syndrome-X, comprising the step of administering to the subject a pharmaceutically effective amount of diazoxide.

In a sixth embodiment, the present invention provides a method for lowering blood pressure in a subject with syndrome-X, comprising the step of administering to the subject a pharmaceutically effective amount of diazoxide.

In a seventh embodiment, the present invention provides a method for treating a diabetic complication in a subject, comprising the step of administering to the subject, a pharmaceutically effective amount of diazoxide.

In a preferred embodiment in a method for treating a diabetic complication in a subject, the diabetic complication is selected from the group consisting of complications of adult-onset diabetes, syndrome-X and other metabolic disorder.

In a preferred embodiment in a method for treating a diabetic complication in a subject, the complication is high proinsulin levels.

In a preferred embodiment in a method for treating a diabetic complication in a subject, the pharmaceutically effective amount of diazoxide is increasing doses of diazoxide until endogenous inulinopenia with ketonuria necessitating exogenous insulin administration appears.

In an eighth embodiment, the present invention provides a method for causing insulin sensitization in a subject, comprising the step of administering to the subject a pharmaceutically effective amount of diazoxide.

The term 'treating' as used herein refers to both preventative treatment, in order to prevent occurrence of the disease and treatment of the disease itself.

The term 'metabolic syndrome' as used herein refers to syndrome-X and any other metabolic syndrome.

DESCRIPTION OF THE PREFERRED EMBODIMENTS

The present invention is of a novel treatment for metabolic syndrome and resulting complications, more preferably the novel treatment is the use of diazoxide for the treatment of syndrome-X and resulting complications that include hyperlipidemia, hypertension, central obesity, hyperinsulinemia and impaired glucose intolerance. Furthermore, the present invention is of the use of diazoxide for preventing and reversing diabetic complications in general, independently of whether the complications are a result of syndrome-X, or adult-onset diabetes. The diabetic complications include excess proinsulin levels.

No effective treatment of syndrome-X is available. Consequently, there is a tremendous need for a treatment such as is provided in the present invention for the use in syndrome-X and resulting complications. Diazoxide is administered to the individual in increasing doses until endogenous inulinopenia with ketonuria necessitating exogenous insulin administration appears. The diazoxide acts to inhibit the release of insulin and proinsulin, lower weight, reduce levels of circulating cholesterol and triglycerides, lower blood pressure and prevent and reverse diabetic complications in subjects with syndrome-X. Furthermore, the diazoxide prevents and reverses diabetic complications in general, independently of whether the complications are from an adult-onset diabetic patient or in subjects with metabolic syndrome. In a normal subject, there is a controlled amount of insulin and a small amount of proinsulin, whereas in a subject with diabetes the reverse is true, such that there is a small amount of insulin and an excess of proinsulin. Diazoxide reduces and can even abolish the high proinsulin levels, causing insulin sensitization, necessitating addition of exogeneous insulin. The effect of diazoxide causing insulin sensitization may be due to this reduction of the over secretion of endogenous insulin and proinsulin, which causes many of the features of to syndrome-X and diabetes complications. Alternatively, the effect of diazoxide may be a direct effect of the diazoxide.

It is to be understood that the invention is not limited in its application to the details of construction and the arrangement of the components set forth in the following description. The invention includes other embodiments and can be practiced or implemented in various ways. Also it is to be understood that the phraseology and terminology employed herein is for the purpose of description only and should not be regarded as limiting.

A pharmaceutically effective amount of diazoxide can be administered to subjects exhibiting syndrome-X or established symptoms, such as hyperlipidemia, hypertension, central obesity, hyperinsulinemia and impaired glucose intolerance, or subjects with diabetes complications and patients at risk. A pharmaceutically effective amount can be defined as administering increasing doses of diazoxide until endogenous insulinopenia with ketonuria necessitating exogenous insulin administration appears. All formulations of diazoxide are possible, however in each case diazoxide is preferably the only active ingredient. Preferably the dose is from about 4 mg to about 15 mg/kg. More preferably the dose is from about 5 mg/kg to about 8 mg/kg and most preferably the dose is about 5 mg/kg. The diazoxide can be administered intravenously, orally, intramuscularly, parenterally, subcutaneously, nasally or rectally. The most preferred route is oral.

The present invention may be better understood with reference to the examples and the accompanying description, which are in no way limiting.

Example 1

The subject was a sixteen year old male, presenting characteristics of syndrome-X. These characteristics included being overweight (125 kg, 180 cm), central obesity and hypertension. Laboratory tests showed hyperlipidemia, impaired glucose tolerance with normal HbAlc, hyperinsulinemia and elevated c-peptide and proinsulin levels. During follow-up, a rapid progressive sensory neuropathy consisting of propioceptive problems (problems of orientation in space), loss of thermal and pain sensation and severe muscle pain was observed. Complete diagnostic procedure including muscle biopsy, because of severe muscle pains revealed normal muscle function and structure. Treatment to alleviate pain with various drugs was unsuccessful. The condition of the subject rapidly deteriorated with severe limitation of daily physical activity.

An increasing dose of oral diazoxide to reach 450 mg a day divided in three doses was administered to the subject. The blood glucose of the subject started to rise with the appearance of glucosuria and ketonuria. At this point the subject was give insulin injections three times a day. The blood glucose of the subject was kept under 200 mg % and ketones disappeared from the urine. Seven weeks after insulin administration, the cholesterol and TG levels of the subject started to decrease, his blood pressure dropped and he lost 5 kg of weight without food restriction. Reversal of thermal and pain insensitivity was observed (Tables 1 and 2) and the subject was also able to do physical activity. In Table 1 fasting/stimulated C-peptide Pmol/l levels are an indication of proinsulin levels. In Table 2, reversal of arm insensitivity values show the amount of area in the arm which is sensitive. The increasing values are indicative of increasing sensitivity. Due to incomplete reversal of pathology the dose of diazoxide was increased to 600 mg/day. A further increase in blood glucose was seen necessitating higher insulin doses. Eight weeks after the dose increase, the subject lost an additional 5 kg and laboratory tests showed complete normalization of cholesterol and TG levels (Tables 1 and 2). Moreover, further improvement of the skin insensitivity threshold of the subject was observed.

TABLE 1

Follow-up, laboratory data

| Date | Cholesterol Mg/dl | TG Mg/dl | Uric acid Mg/dl | Fasting/stimulated C-peptide Pmol/l |
|---|---|---|---|---|
| Aug 1998 | 330 | 1230 | 8.6 | 1476/3941 |
| Oct 1998 | 280 | 500 | 8.0 | 999/2251 |
| Feb 1999 | 160 | 180 | 6.2 | 801/1780 |

TABLE 2

Follow-up, clinical data

| Date | Weight | Reversal of left arm insensitivity (cm) | Reversal of right arm insensitivity (cm) | Daily insulin (U) dose | Daily diazoxide (mg) dose |
|---|---|---|---|---|---|
| Aug 1998 | 125 | 0 | 0 | 0 | 450 |
| Oct 1998 | 120 | 27 | 0 | 98 | 600 |
| Feb 1999 | 115 | 45 | 18 | 98 | 600 |
| March 1999 | 107 | 45 | 38 | 74 | 600 |

It can therefore be concluded that administration of oral diazoxide in the treatment of syndrome-X was effective in causing insulin sensitization, decreasing cholesterol and TG levels, lowering blood pressure, reducing weight and reversing thermal and pain insensitivity.

Example 2:

Possible methods of treatment and compositions for administration for the treatment of syndrome-X and diabetes complications Diazoxide can be administered to a subject in a number of ways, which are well known in the art. For example administration may be done orally, intravenously, subcutaneously, intramuscularly, parenterally, nasally or rectally. The most preferred route is oral.

Diazoxide can be administered to subjects with diagnosed metabolic syndrome or adult-onset diabetes. Additionally, it can be given to subjects at risk, or to those with a symptom indicative of syndrome-X, such as hyperlipidemia, hypertension, central obesity, hyperinsulinemia and impaired glucose intolerance.

Example 3:

Various compositions for the treatment of syndrome-X as well as resulting complications and diabetes complications Compositions for oral administration, which is a preferred route of administration, can be in a form that include powders or granules, suspensions or solutions in water or non-aqueous media, sachets, capsules, tablets, gelcaps and sustained release formulations. Thickeners, diluents, flavorings, vitamins dispersing aids, emulsifiers or binders may be desirable.

All kinds of pharmaceutical compositions administerable by subcutaneous routes can be advantageously used in the present invention.

Compositions for intravenous administration, can be in a form that includes liquid suspensions or solutions in water or non-aqueous media.

Dosing is dependent on the responsiveness of the subject to diazoxide. Preferably the dose is from about 4 mg to about 15 mg/kg. More preferably the dose is from about 5 mg/kg to about 8 mg/kg and most preferably the dose is about 5 mg/kg. The amount received by the subject is controlled. For example as a pill, the dose and frequency of dosing would be dependent on the responsiveness of the subject. Persons of ordinary skill in the art can easily determine optimum dosages, dosing methodologies and repetition rates.

It will be appreciated that the above examples and descriptions are intended only to serve as examples, and that many other embodiments are possible within the spirit and the scope of the present invention.

REFERENCES CITED

1. Altszuler, N. Diabetes, 26:931, 1977.
2. Henquin et al. Diabetes, 31:766–783, 1982.
3. Stanely, C. A. Adv. Ped., 23:315, 1976.
4. Reaven, G. Role of insulin resistance in human disease. Diabetes. 37:1595–1607, 1988
5. Ferrannini, E. et al. Hyperinsulinemia: the key feature of a cardiovascular and metabolic syndrome. Diabetologia. 34:416–422, 1991.

What is claimed is:

1. A method for treating syndrome-X and resulting complications in a subject in need thereof, comprising the step of administering to the subject, a pharmaceutically effective amount of diazoxide to interfere with pancreatic islet function, by ablating endogenous insulin secretion, resulting in a state of insulin deficiency and high blood glucose levels equivalent to that of diabetic patients that depend on exogenous insulin administration for normalization of their blood glucose levels.

2. The method of claim 1, wherein said complication is selected from the group consisting of central obesity, hyperlipidemia, hyperinsulinemia, hypertension and impaired glucose tolerance.

3. The method of claim 1, wherein said pharmaceutically effective amount is from about 4 mg/kg to about 15 mg/kg.

4. The method of claim 1, wherein said pharmaceutically effective amount is from about 5 mg/kg to about 8 mg/kg.

5. The method of claim 1, wherein the preferred route of administration is oral.

6. The method of claim 5, wherein said diazoxide is provided in a tablet form.

7. The method of claim 1, wherein said diazoxide is provided in an intravenous form.

8. The method of claim 1, wherein said diazoxide is administered until endogenous insulin levels are lowered.

9. The method of claim 8, wherein exogenous insulin must be administered.

10. The method of claim 1, wherein said diazoxide decreases proinsulin levels.

11. The method of claim 1, wherein said diazoxide decreases proinsulin and insulin precursor levels.

12. A method for prophylactic treatment of syndrome-X in a subject in need thereof, comprising the step of administering to the subject a pharmaceutically effective amount of diazoxide to interfere with pancreatic islet function, by ablating endogenous insulin secretion, resulting in a state of insulin deficiency and high blood glucose levels equivalent to that of diabetic patients that depend on exogenous insulin administration for normalization of their blood glucose levels.

13. A method for reducing weight in a subject with syndrome-X, comprising the step of administering to the subject a pharmaceutically effective amount of diazoxide to interfere with pancreatic islet function, by ablating endogenous insulin secretion resulting in a state of insulin deficiency and high blood glucose levels equivalent to that of diabetic patients that depend on exogenous insulin administration for normalization of their blood glucose levels.

14. A method for reducing the levels of circulating cholesterol and triglycerides in a subject with syndrome-X, comprising the step of administering to the subject a pharmaceutically effective amount of diazoxide to interfere with pancreatic islet function, by ablating endogenous insulin secretion resulting in a state of insulin deficiency and high blood glucose levels equivalent to that of diabetic patients diabetic patients that depend on exogenous insulin administration for normalization of their blood glucose levels.

15. A method for lowering blood pressure in a subject with syndrome-X, comprising the step of administering to the subject a pharmaceutically effective amount of diazoxide to interfere with pancreatic islet function, by ablating endogenous insulin secretion, resulting in a state of insulin deficiency and high blood glucose levels equivalent to that of diabetic patients that depend on exogenous insulin administration for normalization of their blood glucose levels.

16. A method for treating a diabetic complication in a subject in need thereof, comprising the step of administering to the subject, a pharmaceutically effective amount of diazoxide to interfere with pancreatic islet function, by ablating endogenous insulin secretion, resulting in a state of insulin deficiency and high blood glucose levels equivalent to that of diabetic patients that depend on exogenous insulin administration for normalization of their blood glucose levels.

17. The method of claim 16, wherein said diabetic complication is selected from the group consisting of complications of adult-onset diabetes, syndrome-X and other metabolic disorders.

18. The method of claim 16, wherein said complication is high proinsulin levels.

19. A method for treating a diabetic complication in a subject in need thereof, comprising the step of administering to the subject, a pharmaceutically effective amount of diazoxide to interfere with pancreatic islet function, by ablating endogenous insulin secretion, resulting in a state of insulin deficiency and high blood glucose levels equivalent to that of diabetic patients that depend on exogenous insulin administration for normalization of their blood glucose levels, wherein said pharmaceutically effective amount of diazoxide is from about 4 mg/kg to about 8 mg/kg of diazoxide until endogenous insulinopenia with ketonuria necessitating exogenous insulin administration appears.

20. A method for causing insulin sensitization in a subject in need thereof, comprising the step of administering to the subject a pharmaceutically effective amount of diazoxide to interfere with pancreatic islets function, by ablating endogenous insulin secretion resulting in a state of insulin deficiency and high blood glucose levels equivalent to that of diabetic patients that depend on exogenous insulin administration for normalization of their blood glucose levels.

21. A method for treating diabetic neuropathy in a subject in need thereof, comprising the step of administering to the subject, a pharmaceutically effective amount of diazoxide.

22. A method for treating a diabetic complication in a subject in need thereof, comprising the step of administering to the subject, a pharmaceutically effective amount of diazoxide, wherein said pharmaceutically effective amount of diazoxide is from about 4 mg/kg to about 8 mg/kg of diazoxide until endogenous insulinopenia with ketonuria necessitating exogenous insulin administration appears.

23. A method for reducing the release of insulin and insulin precursors in a subject with syndrome-X, comprising the step of administering to the subject a pharmaceutically effective amount of diazoxide to interfere with pancreatic islets function, by ablating endogenous insulin secretion resulting in a state of insulin deficiency and high blood glucose levels equivalent to that of diabetic patients that depend on exogenous insulin administration for normalization of their blood glucose levels.

* * * * *